United States Patent
Fujiyama et al.

(10) Patent No.: US 8,851,737 B2
(45) Date of Patent: Oct. 7, 2014

(54) RUBBER EXTRUDER AND METHOD OF SAMPLING EXTRUDED RUBBER

(75) Inventors: Kouta Fujiyama, Tokyo (JP); Yuuki Nakai, Tokyo (JP); Shohei Koyama, Tokyo (JP)

(73) Assignee: Bridgestone Corporation, Tokyo (JP)

(*) Notice: Subject to any disclaimer, the term of this patent is extended or adjusted under 35 U.S.C. 154(b) by 119 days.

(21) Appl. No.: 13/265,930

(22) PCT Filed: Apr. 30, 2010

(86) PCT No.: PCT/JP2010/057661
§ 371 (c)(1),
(2), (4) Date: Nov. 18, 2011

(87) PCT Pub. No.: WO2010/126126
PCT Pub. Date: Nov. 4, 2010

(65) Prior Publication Data
US 2012/0063259 A1 Mar. 15, 2012

(30) Foreign Application Priority Data
Apr. 30, 2009 (JP) ................................. 2009-111324

(51) Int. Cl.
B29C 47/74 (2006.01)
B29C 47/00 (2006.01)
G01N 1/20 (2006.01)
B29C 47/92 (2006.01)
B29C 47/36 (2006.01)
B29B 7/42 (2006.01)
B29K 21/00 (2006.01)

(52) U.S. Cl.
CPC ............. B29B 7/424 (2013.01); B29C 47/0021 (2013.01); *B29C 47/74* (2013.01); *B29C 2947/92885* (2013.01); *B29C 2947/92876* (2013.01); G01N 1/20 (2013.01); *B29C 2947/92828* (2013.01); B29C 47/92 (2013.01); B29C 47/364 (2013.01); *B29C 2947/9259* (2013.01); *B29C 2947/926* (2013.01); *B29C 47/367* (2013.01); *B29C 2947/92514* (2013.01); B29B 7/42 (2013.01); *B29K 2021/00* (2013.01)
USPC ............................................. 366/77; 366/140

(58) Field of Classification Search
CPC .......................... B29C 47/367; B29C 47/6012
USPC .................. 366/75, 76.92, 76.93, 77, 79, 140
See application file for complete search history.

(56) References Cited

U.S. PATENT DOCUMENTS 2,211,638 A * 8/1940 Benz .............................. 425/575
3,191,229 A * 6/1965 Vanzo ........................... 425/208
(Continued)

FOREIGN PATENT DOCUMENTS

JP      A-60-137609      7/1985
JP      A-5-131521       5/1993
(Continued)

OTHER PUBLICATIONS

International Preliminary Report on Patentability dated Dec. 12, 2011 issued in International Application No. PCT/JP2010/057661.

(Continued)

*Primary Examiner* — Charles Cooley
*Assistant Examiner* — Abbas Rashid
(74) *Attorney, Agent, or Firm* — Oliff PLC

(57) ABSTRACT

In a rubber extruder, a rubber sample is sampled while the rubber extruder is operating. In a rubber extruder formed of a cylinder and a screw arranged in the cylinder, a rubber sample taking-out path is provided in the vicinity of an outlet-side end portion of the screw and in front of a rubber taking-in port of a pair of gears of a gear pump. A path opening/closing means including a ball valve which opens/closes the rubber sample taking-out path is also provided so that a part of rubber extruded by the screw is taken out as a sample by opening/closing the ball valve at predetermined timing.

5 Claims, 4 Drawing Sheets

(56) References Cited

U.S. PATENT DOCUMENTS

| | | | | |
|---|---|---|---|---|
| 3,352,952 | A * | 11/1967 | Marr | 264/40.4 |
| 3,638,921 | A * | 2/1972 | Bredeson et al. | 241/60 |
| 3,738,618 | A * | 6/1973 | Hehl | 366/79 |
| 3,998,439 | A * | 12/1976 | Feix | 366/76.91 |
| 4,060,226 | A * | 11/1977 | Schweller | 366/75 |
| 4,124,308 | A * | 11/1978 | Sokolow | 366/77 |
| 4,183,673 | A * | 1/1980 | Easley et al. | 366/76.2 |
| 4,247,501 | A * | 1/1981 | Easley et al. | 264/77 |
| 4,290,701 | A * | 9/1981 | Schad | 366/77 |
| 4,310,251 | A * | 1/1982 | Scharer et al. | 366/77 |
| 4,395,130 | A * | 7/1983 | Kutowy | 366/137 |
| 4,448,736 | A | 5/1984 | Emery et al. | |
| 4,764,020 | A * | 8/1988 | Moriyama | 366/76.4 |
| 4,822,269 | A * | 4/1989 | Kamiyama et al. | 425/203 |
| 4,959,186 | A * | 9/1990 | Dollhopf et al. | 264/102 |
| 5,024,531 | A * | 6/1991 | Will | 366/75 |
| 5,232,280 | A * | 8/1993 | Moriyama | 366/83 |
| 5,662,415 | A * | 9/1997 | Gisko | 366/139 |
| 6,030,203 | A * | 2/2000 | Kuroda | 425/561 |
| 6,609,819 | B2 * | 8/2003 | Hauck et al. | 366/85 |
| 6,638,051 | B2 * | 10/2003 | Yamaguchi et al. | 425/204 |
| 7,322,738 | B2 * | 1/2008 | Yamane et al. | 366/75 |
| 7,361,294 | B2 * | 4/2008 | Pierick et al. | 264/50 |
| 8,137,600 | B2 * | 3/2012 | Pierick et al. | 264/45.1 |
| 2005/0163881 | A1 * | 7/2005 | Pierick et al. | 425/4 R |
| 2008/0050576 | A1 * | 2/2008 | Pierick et al. | 428/304.4 |

FOREIGN PATENT DOCUMENTS

| | | |
|---|---|---|
| JP | A-2001-150515 | 6/2001 |
| JP | B2 3375398 | 2/2003 |
| JP | A-2007-171117 | 7/2007 |

OTHER PUBLICATIONS

International Search Report mailed on Jul. 13, 2010 issued in International Application No. PCT/JP2010/057661.

* cited by examiner

RUBBER EXTRUDER AND METHOD OF SAMPLING EXTRUDED RUBBER

TECHNICAL FIELD

The present invention relates to a rubber extruder and a method of sampling rubber extruded by the rubber extruder.

BACKGROUND ART

In general, a tire is formed of a plurality of rubber members for a tire and each portion such as an inner liner, a tread portion, a side wall portion and the like is formed of unvulcanized rubber according to characteristics required for each of them. The rubber members constituting each portion of the tire is formed by extruding the rubber member using a rubber extruder provided with a die in compliance with the sectional shape of the respective rubber members and cutting the extruded unvulcanized rubber into a predetermined length or wrapping it around a tire molding drum, for example.

FIG. 5 is a sectional view of a prior-art rubber extruder described in Patent Document 1.

This rubber extruder 100 includes a hopper 113 which inputs rubber together with a material to be kneaded, a screw 111 which transfers the rubber having been inputted into this hopper 113 while kneading it, a cylinder 112, a gear pump 122 formed of two gears 122a and bearings 122b thereof, and a die head 124 which forms the extruded rubber into a desired sectional shape.

In this rubber extruder, the rubber having been inputted from the hopper 113 is transferred by the rotating screw 111 and discharged into a rubber retaining portion 115, and the rubber having been retained in the rubber retaining portion 115 once is extruded by the gear pump 122 by a constant amount each into a predetermined shape through the die head 124.

A sample is taken in order to check the physical properties and states of the rubber extruded by the rubber extruder as above. Particularly, if ribbon-shaped rubber having a small width of 100 mm or less is to be continuously extruded, the line is stopped, and a part of the ribbon-shaped rubber is carefully cut out by using a knife by a manual work while attention is paid not to cut the rubber.

However, with such a method, the sampling work is cumbersome and moreover, since the line should be stopped, it is a cause to obstruct productivity improvement. Particularly, in a design in which a process of supplying rubber of a rubber extruder directly to a molding machine is adopted, since the rubber extruder cannot be stopped in the middle, there is a problem that sampling cannot be performed. Also, since the sampling relies on manual work, it is likely that troubles relating to the quality of a molded tire such that a cut-out sample is mistaken, the rubber type is wrong or the like can be induced, while workers should enter information relating to the cut-out samples one by one, which results in a problem of an increase in the number of working processes.

Here, regarding automatic sampling of extruded rubber, such a device is known which performs a series of operations in which a sample piece is taken from a continuously extruded rubber sheet and the sample piece is delivered to a measuring device (See Patent Document 2), for example.

FIG. 6 is a diagram schematically illustrating this sampling device.

In this sampling device 101, a rubber sheet G extruded from a rubber extruder (not shown) is made to pass between a cutter receiver 102 and a punching cutter 104 arranged above that and capable of elevation, and the cutter 104 is lowered so as to punch the rubber sheet G between it and the cutter receiver 102, and the punched rubber sheet G is contained in a cylindrical hole in the cutter 104 once, and then, the sample piece in the cylindrical hole is sucked by a vacuum pad 106 at a sample receiving position P1 immediately below the cutter 104, while sample receiving means 105 transfers this to a sample delivery position of a turn table 107 provided in a sample measuring means 103

However, this sampling device 101 basically replaces the prior-art manual work of cutting the rubber sheet G after being extruded by an automatic work by machine, and since a part of the extruded rubber sheet is cut out, the rest of the cut-out part remains as it is and moreover, a cutting device which cuts out and samples a rubber sample should be provided separately from the rubber extruder. Therefore, not only the cost but also the size of the device is increased, and there is another problem that a place for installing the cutting device is needed.

PRIOR-ART REFERENCES

Patent Document

Patent Document 1: Japanese Unexamined Patent Application Publication No. 2001-150515
Patent Document 2: Japanese Unexamined Patent Application Publication No. 2007-171117

SUMMARY OF INVENTION

Problems to be Solved by the Invention

The present invention was made in order to solve the above prior-art problems and has an object to enable sampling of rubber sample regardless of extruded rubber and moreover with a simple configuration without increasing the size of the device.

Means for Solving the Problems (1) A rubber extruder of the present invention is a rubber extruder formed of a cylinder and a screw arranged in the cylinder for pressurizing and kneading inputted rubber, characterized in that a rubber sample taking-out path through which a part of rubber extruded by the screw is taken out as a rubber sample is provided on an outlet-side end portion of the cylinder or on the downstream side from the outlet-side end portion and a path opening/closing means which opens/closes the rubber sample taking-out path is provided.

(2) The rubber extruder of the present invention is characterized in that the rubber extruder described in the above (1) is provided with a gear pump and the rubber sample taking-out path is provided between the outlet-side end portion of the cylinder and the gear pump.

(3) The rubber extruder of the present invention is characterized in that, in the rubber extruder described in the above (1) or (2), a sampling device mounted at the outlet-side end portion of the cylinder and having a center hole which becomes a path for the rubber extruded from the cylinder at the center part and the rubber sample taking-out path on the inner peripheral surface of the center hole, respectively, and provided with a path opening/closing means which opens/closes the rubber sample taking-out path is provided.

(4) The rubber extruder of the present invention is characterized in that, in the rubber extruder described in any of the above (1) to (3), the path opening/closing means is provided with a ball valve mechanism.

(5) The rubber extruder of the present invention is characterized in that, in the rubber extruder described in any of the above (1) to (4), a driving mechanism is provided which automatically operates the path opening/closing means at predetermined timing.

(6) A method of sampling extruded rubber of the present invention is characterized by having a step of inputting rubber into the rubber extruder, a step of pressurizing the inputted rubber while kneading and transferring it, and a step of branching and sampling a part of the pressurized rubber as a sample at predetermined timing on an outlet-side end portion of the cylinder of the rubber extruder or on the downstream side from the outlet-side end portion.

Advantages of the Invention

According to the present invention, extruded rubber can be sampled freely at arbitrary timing without increasing the size of the device as before and moreover without affecting the extruded rubber at all.

DESCRIPTION OF EMBODIMENTS

A rubber extruder of the present invention and a method of sampling extruded rubber using the rubber extruder will be described by referring to the attached drawings.

Figure 1:
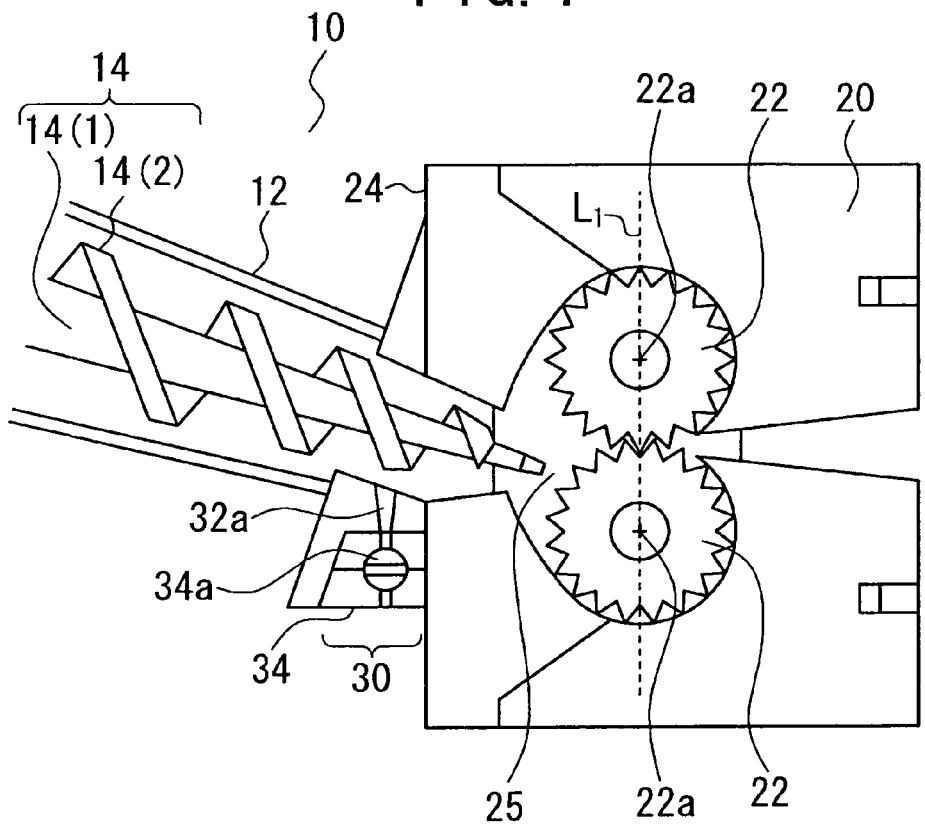
FIG. 1 is a sectional view of an essential part of a rubber extruder according to a first embodiment of the present invention.

FIG. 1 is a sectional view of an essential part of a rubber extruder according to a first embodiment of the present invention.

As illustrated, a rubber extruder (compression-screw rubber extruder) 10 is formed of a screw 14 contained in a cylinder 12 and a gear pump 20 mounted on the distal end side (outlet side) of the cylinder 12, and the screw 14 is formed of a screw shaft 14(1) and a spiral blade portion 14(2) provided on the outer periphery of the screw shaft 14(1). This rubber extruder 10 transfers feed rubber having been inputted from the hopper (not shown) similarly to the prior-art device toward the distal end of the cylinder 12 while rotating and driving the screw 14 by a driving device (not shown) for kneading.

In the illustrated embodiment, the diameters of the cylinder 12 and the screw 14 are gradually reduced toward the distal ends, and the screw shaft 14(1) is not perpendicular to but inclined with respect to a line $L_1$ which connects gear shafts 22a of a pair of gears 22 of the gear pump 20, that is, extends from the upper left to the lower right in the figure.

Here, the pitch of the blade portion 14(2) of the screw 14 is constant, and since the rubber transferred through the cylinder 12 is pushed into a path which becomes narrower toward the distal end of the cylinder 12, the pressure is gradually boosted toward the distal end side (outlet side).

In this embodiment, the distal end portion (outlet-side portion) of the screw 14 reaches the vicinity of a rubber taking-in port of the pair of gears 22 of the gear pump 20 in a rubber retaining portion 25.

Here, between the distal end surface of the cylinder 12 extending toward the lower right in the figure and a perpendicular mounting surface 24 of a cylinder-side casing of the gear pump 20, a sampling device 30 connected to the both in an airtight manner and from which a part of rubber around the distal end portion of the screw 14 is taken out as a sample is arranged.

Figure 2A:
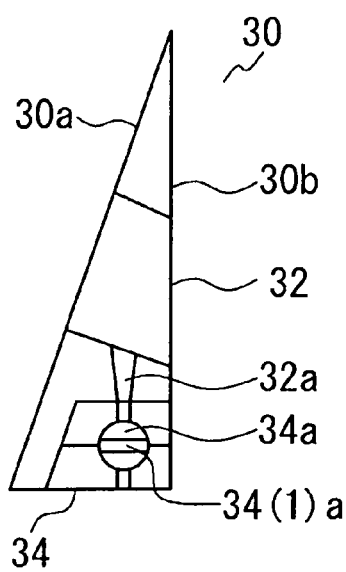
FIGS. 2A and 2B are sectional views schematically illustrating a rubber sampling device in the rubber extruder illustrated in FIG. 1.
Figure 2B:
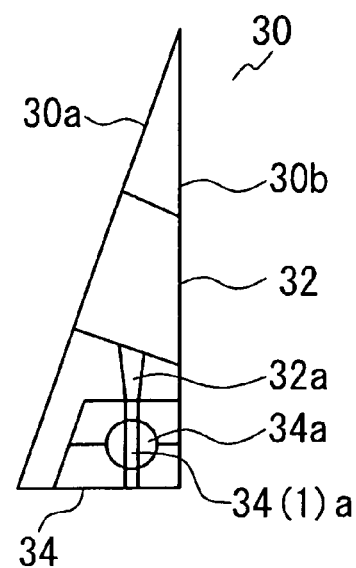

FIGS. 2A and 2B are cross sectional views of the sampling device 30, in which FIG. 2A illustrates a closed position of a ball valve 34a, which is an opening/closing means of a path opening/closing device 34 provided in the sampling device 30 and FIG. 2B illustrates an open position of the same.

In the sampling device 30, a section provided with a surface 30a on the cylinder 12 side perpendicular to the screw shaft 14(1) and a surface 30b in parallel with the mounting surface 24 on the cylinder side of the gear pump 20 forms a substantially triangular shape so that the distal end surface of the cylinder 12 and the perpendicular mounting surface 24 of the cylinder-side casing of the gear pump 20 can be connected to each other in an airtight manner, and the screw 14 projecting from the cylinder 12 penetrates the center part thereof. That is, the sampling device 30 has a screw hole 32, which is a center hole which becomes a path for rubber extruded from the cylinder 12, a path 32a for sampling, provided on the lower peripheral face of the screw hole 32 in the figure and having the other end opened to the side of outside air, and the path opening/closing device 34 including, for example, the ball valve 34a provided in the opening of this path 32a.

The ball valve 34a itself is well-known and opens/closes the path 32a by rotating a ball of the ball valve 34a and a path 34(1)a provided in the ball by 90° by rotating operating means (an operation lever, for example), not shown. That is, by rotating the operation lever, for example, the ball valve 34a is opened, and the path 32a is made to communicate with the outside air. As a result, a part of rubber pressurized on the distal end side of the screw 14 is extruded to the outside through the path opening/closing device 34 from the path 32a due to a pressure difference from the atmosphere and taken as a rubber sample.

When a predetermined amount of the rubber sample has been taken, the ball valve 34a is operated so as to shut off the path 32a.

Therefore, in this embodiment, labor of a worker to cut off rubber extruded by the gear pump with a knife as before is not required, but only with a simple operation of opening/closing the ball valve 34a, a sample of feed rubber can be taken out easily and reliably.

Also, since the path 32a for sampling is provided on the downstream side of the cylinder 12, the internal pressure of the feed rubber has reached a pressure which is sufficiently high for taking out of a sample and also, since kneading has been substantially finished, a rubber sample substantially equal in the physical properties and states to the rubber discharged from the gear pump 20 can be obtained.

By taking out a rubber sample, a rubber pressure in the rubber retaining portion 25 might be slightly lowered, but a rubber amount in sampling is slight as compared with the entire feed rubber amount, and since the internal pressure of the feed rubber can be adjusted by adjusting the rotation speed of the screw 14, substantial pressure drop does not occur. Also, as a result, the sampling speed can be freely adjusted.

Also, the position of the path 32*a* for sampling is arranged on the upstream side of the pair of gears 22 of the gear pump 20 in the rubber conveying direction, that is, on the front side, and thus, the pressure of rubber in the rubber retaining portion 25 can be adjusted also by adjusting the rotation speed of the gears 22, and thus, the sampling speed can be also adjusted by this, which is advantageous.

In this embodiment, even if the rubber pressure somewhat fluctuates in the rubber retaining portion 25, the rubber pressure to be discharged can be adjusted constant by the gear pump 20.

Moreover, in the above description, the sampling device 30 has a substantially triangular cross-sectional shape due to a relationship between arrangement positions of the screw shaft 14(1) and the perpendicular mounting surface 24 on the cylinder-side casing of the gear pump 20, but in a configuration in which the screw shaft 14(1) is orthogonal to the mounting surface 24, for example, the section is formed in a substantially rectangular shape.

Figure 3:
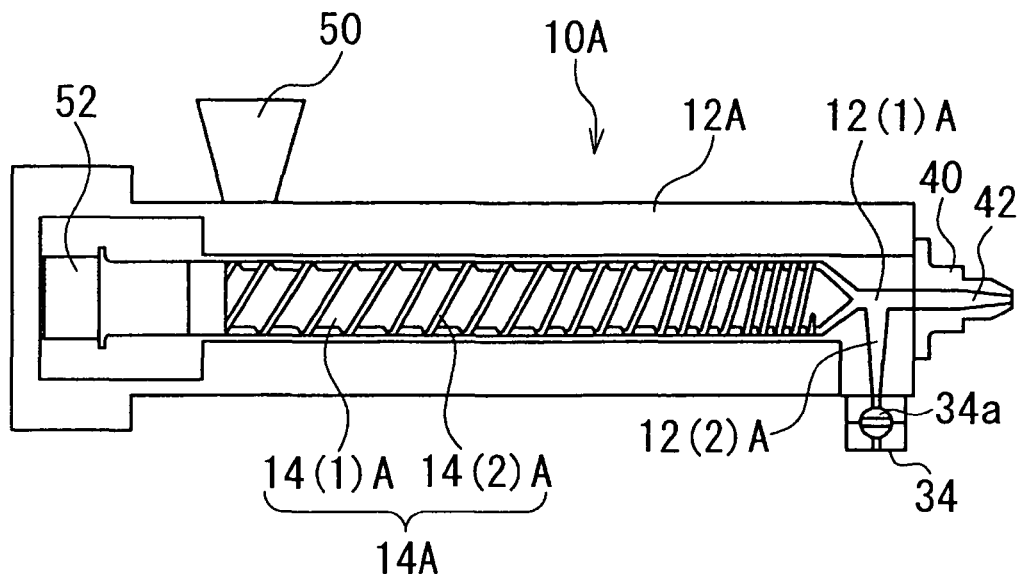
FIG. 3 is a sectional view illustrating a rubber extruder according to a second embodiment of the present invention.

FIG. 3 is a sectional view of a rubber extruder (compression-screw rubber extruder) 10A according to a second embodiment of the present invention.

This rubber extruder 10A does not have a gear pump, unlike the rubber extruder 10 of the first embodiment. That is, the rubber extruder 10A includes a cylinder 12A, a screw 14A rotatably supported inside the cylinder 12A, a die 40 mounted at the distal end of the cylinder 12A (right side in the figure), a hopper 50 provided on the upper side of the rear part of the cylinder 12A (left in the figure), and a rotation driving device 52 such as a motor which rotates the screw 14A.

The screw 14A is formed of a screw shaft 14(1)A and a spiral blade portion 14(2)A provided on the outer periphery thereof.

The screw 14A is formed of five stages of screws, each having a different capacity of a phase space of feed rubber per unit time by the screw 14A, that is, a different pitch of the blade portion 14(2)A or five stages of screws from the first-stage screw on the rear end side (left end side in the figure) to the fifth-stage screw on the front end side (right end side in the figure). Thus, the rubber inputted from the hopper 50 has its internal pressure gradually raised to a predetermined pressure at the outlet while it is kneaded and transferred by the screw 14A.

At the distal end side (outlet side) of the cylinder 12A, a path 12(2)A for sampling, opened in the peripheral wall of a path 12(1)A communicating with a path 42 of the die 40 of the screw 14A is formed. At the outlet side on the peripheral surface of the cylinder 12A of the path 12(2)A, the path opening/closing device 34 provided with the ball valve 34*a* similar to the description in the first embodiment is integrally mounted on the outer periphery of the cylinder 12A.

By means of this configuration, similarly to the first embodiment, by rotating the ball valve 34*a* of the path opening/closing device 34 by arbitrary means such as a lever, not shown, and by opening the path 12(2)A to the outside air, a part of the pressurized rubber can be taken out as a sample through the path 12(2)A and the path opening/closing device 34 by means of the pressure thereof.

Since the pressure applied to the feed rubber can be raised by an increase in the number of stages and rotation number of the screw 14A, the pressure of the feed rubber and hence, the sampling speed can be freely adjusted in this case, too.

Also, since the path 12(2)A for sampling is provided on the outlet-side end portion of the cylinder 12A, the internal pressure of the feed rubber has reached a pressure high enough for taking out the sample, and kneading has been fully finished, and thus, a rubber sample substantially equal in the physical properties and states to the rubber discharged from the die 40 can be obtained.

Figure 4:
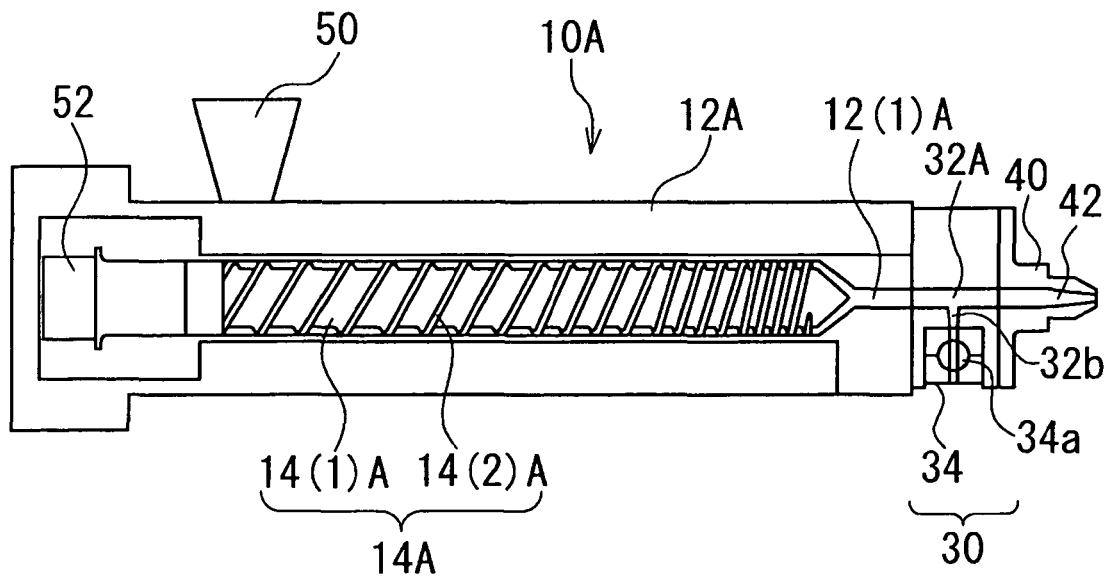
FIG. 4 is a sectional view illustrating a rubber extruder according to a third embodiment of the present invention.
Figure 5:
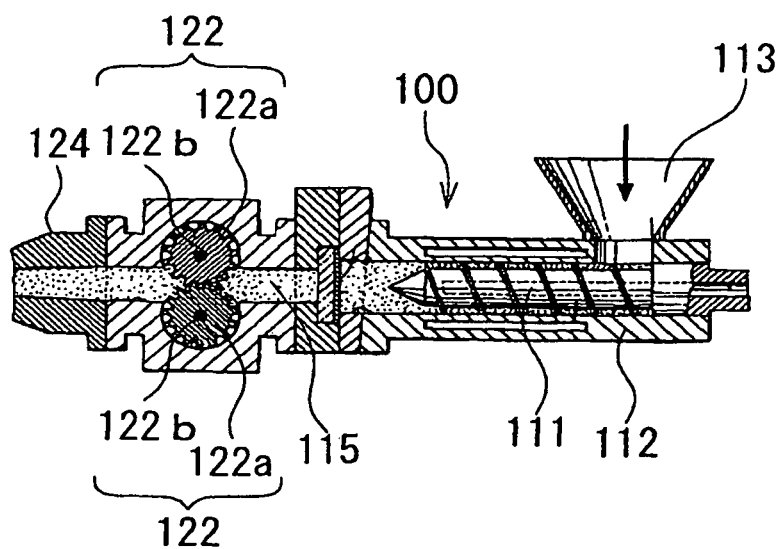
FIG. 5 is a sectional view illustrating a prior-art rubber extruder.
Figure 6:
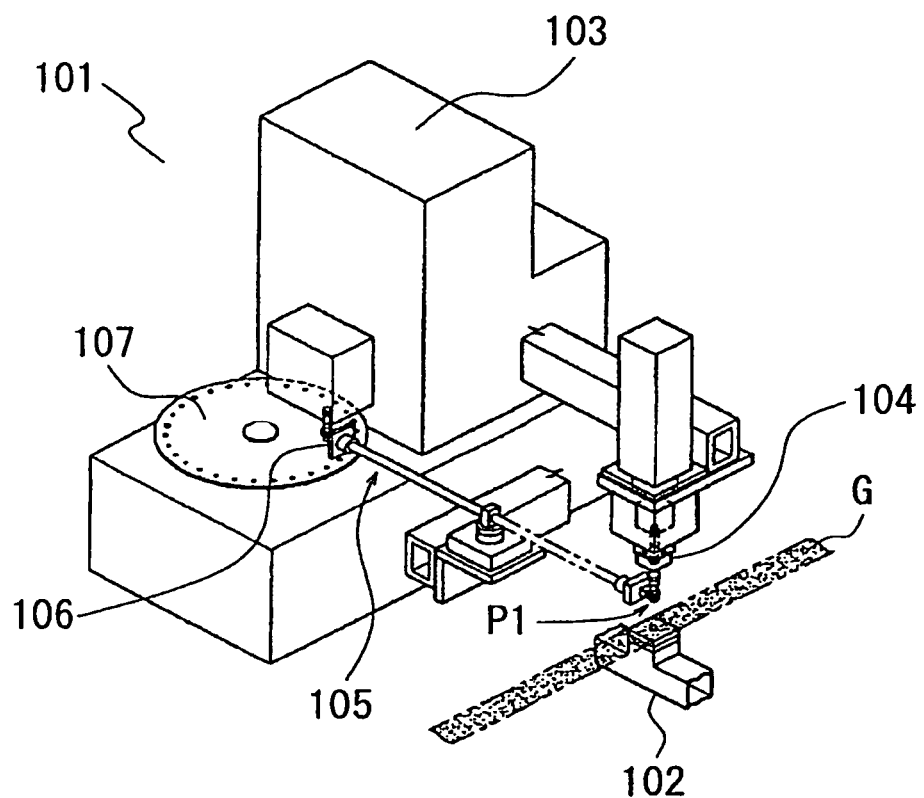
FIG. 6 is a perspective view illustrating a prior-art sampling device of extruded rubber.

FIG. 4 is a sectional view illustrating a rubber extruder according to a third embodiment, which is basically similar to the rubber extruder according to the second embodiment (compression-screw rubber extruder) 10A, but here, the sampling device 30 is formed separately from the cylinder 12A similarly to the first embodiment and interposed between the extruding cylinder 12A and the die 40. The sampling device 30 has a path 32A which connects the path 12(1)A of the cylinder 12A and a path 42 leading to the outlet of the die 40 to each other at the center part, provided with a path 32*b* for sampling opened in the path 32A at this center part and having the other end opened to the side of the outside air, and the cross-sectional shape thereof is a substantially rectangular shape as illustrated. On the outlet side of the path 32*b*, the path opening/closing device 34 provided with the ball valve 34*a* similar to the description in the first embodiment is mounted.

By configuring the sampling device 30 as above, the sampling device 30 can be mounted to the existing rubber extruder 10A as it is without applying work to the cylinder 12A side.

According to this embodiment, since the path 32*b* for sampling is provided on the downstream side of the cylinder 12A, internal pressure of the feed rubber has reached a pressure high enough for taking out a sample, and kneading by the screw 14A has been finished, and thus, a rubber sample substantially equal in the physical properties and states to the rubber discharged from the die 40 can be obtained.

In each of the above embodiments, description was made that the ball valve 34*a* is switched by rotating a manual lever, but the switching may be made automatically.

That is, the ball valve is rotated by an arbitrary mechanism using a controller, not shown, and a driving means such as a small-sized motor, for example. The sampling timing can be freely set in the controller.

Also, at the same time, the sampled rubber is contained in a container, and transferred by appropriate means, for example, being placed on a conveyer as it is to an inspecting device or is dropped into a container intermittently moved at the sampling timing and transferred to the inspecting device and moreover, transferred by arbitrary means such as a vacuum pad described in Patent Document 2, for example, to the inspecting device.

By automatically transferring the sample to an inspection position, the rubber sample can be measured in accordance with the sampling order, and the rubber sample is not mixed up. Moreover, it may also be so configured that the controller is interlocked with the inspecting device so that an inspection result is stored in a storage means, outputted by an output means or displayed by a display means.

Subsequently, a method of sampling in the rubber extruder for rubber, provided with the above-described sampling device will be described.

First, rubber (raw rubber) is inputted into a hopper of the rubber extruder (Step 1). Then, the inputted rubber is transferred while being kneaded by the screw in the cylinder of the rubber extruder, and the pressure thereof is gradually raised (Step 2). In the vicinity of the outlet of the screw, a part of the rubber having been transferred and kneaded at predetermined timing is branched to a path provided on the peripheral wall of the rubber path on the outlet-side end portion of the cylinder or on the downstream side from the outlet-side end portion and capable of being opened/closed to the outside air and sampled (Step 3), and the rubber taken out as above is transferred to the inspecting device.

The sampling is performed while the screw of the rubber extruder or the screw and the gear pump in the case of the rubber extruder with a gear pump is operating but can be performed during stop if the pressure of the rubber is maintained.

The embodiments of the present invention have been described, but the opening/closing means of the path opening/closing device 34 does not necessarily have to be a ball valve and may be an electromagnetic valve, for example, or any valve as long as the path for sampling rubber can be opened/closed.

EXPLANATION OF REFERENCE NUMERALS

10, 10A rubber extruder
12, 12A cylinder
12(1)A, 12(2)A path
14, 14A screw
14(1), 14(1)A screw shaft
14(2), 14(2)A blade portion
20 gear pump
22 gear
22a gear shaft
24 mounting surface
25 rubber retaining portion
30 sampling device
32 screw hole
32a, 32b path (for sampling)
34 path opening/closing device
34 ball valve
34(1)a path for ball valve
40 die
42 path (for die)
50 hopper
52 driving device (motor).

The invention claimed is:

1. A rubber extruder for pressurizing and kneading inputted rubber, comprising:
    a cylinder and a screw arranged in the cylinder; and
    a sampling device mounted on an outlet-side end portion of the cylinder and having a center hole which becomes a path for rubber extruded from the cylinder at the center part and a rubber sample taking-out path on an inner peripheral surface of the center hole, respectively, and provided with a path opening/closing means which opens/closes the rubber sample taking-out path, wherein
    a path opening/closing means which opens/closes the rubber sample taking-out path is provided; and
    diameters of the cylinder and the screw are gradually reduced toward the distal ends,
    the distal end portion of the screw reaches the vicinity of a rubber taking-in port of a pair of gears of a gear pump,
    a screw shaft is inclined with respect to a line which connects gear shafts of the pair of gears of the gear pump, and
    the sampling device is provided with a surface on the cylinder side perpendicular to the screw shaft and a surface in parallel with a mounting surface on the cylinder side of the gear pump in a sectional shape thereof, and forms a substantially triangular shape, and the screw projecting from the cylinder penetrates the center part thereof.

2. The rubber extruder according to claim 1, further comprising:
    a driving mechanism which automatically operates the path opening/closing means at predetermined timing.

3. A method of sampling extruded rubber from the rubber extruder according to claim 1, comprising the steps of:
    inputting rubber into a rubber extruder having a cylinder and a screw arranged in the cylinder, diameters of the cylinder and the screw being gradually reduced toward the distal ends;
    pressurizing the inputted rubber while kneading and transferring the same; and
    branching and sampling a part of the pressurized rubber as a sample at predetermined timing through a rubber sample taking-out path provided between an outlet-side end portion of the cylinder and a gear pump mounted on the outlet-side of the cylinder.

4. The rubber extruder according to claim 1, wherein
    the path opening/closing means is provided with a ball valve mechanism.

5. The rubber extruder according to claim 4, further comprising:
    a driving mechanism which automatically operates the path opening/closing means at predetermined timing.

* * * * *